(12) United States Patent
Liu et al.

(10) Patent No.: US 11,253,617 B2
(45) Date of Patent: Feb. 22, 2022

(54) ONE STEP 64CU-BABASAR-RGD2 PRODUCTION METHOD

(71) Applicant: UNIVERSITY OF SOUTHERN CALIFORNIA, Los Angeles, CA (US)

(72) Inventors: Shuanglong Liu, Monterey Park, CA (US); Peter Conti, Pasadena, CA (US)

(73) Assignee: University of Southern California, Los Angeles, CA (US)

(*) Notice: Subject to any disclaimer, the term of this patent is extended or adjusted under 35 U.S.C. 154(b) by 174 days.

(21) Appl. No.: 16/205,985

(22) Filed: Nov. 30, 2018

(65) Prior Publication Data

US 2019/0240359 A1    Aug. 8, 2019

Related U.S. Application Data

(60) Provisional application No. 62/593,723, filed on Dec. 1, 2017.

(51) Int. Cl.
*A61K 51/08* (2006.01)
*A61K 51/12* (2006.01)
*A61K 51/04* (2006.01)

(52) U.S. Cl.
CPC ........ *A61K 51/082* (2013.01); *A61K 51/0446* (2013.01); *A61K 51/0482* (2013.01); *A61K 51/0497* (2013.01); *A61K 51/088* (2013.01); *A61K 51/121* (2013.01); *A61K 51/1241* (2013.01); *A61K 2123/00* (2013.01)

(58) Field of Classification Search
CPC ...... A61K 51/00; A61K 51/08; A61K 51/082; A61K 51/088; A61K 51/121; A61K 51/1241; A61K 51/0497; A61K 51/0446; A61K 51/0482; A61K 2121/00; A61K 2123/00
USPC ...... 424/1.11, 1.65, 1.69, 9.1, 9.2; 534/7–16
See application file for complete search history.

(56) References Cited

U.S. PATENT DOCUMENTS 8,536,301 B2 *    9/2013   Cochran ............ A61K 49/0056
                                                  530/324

OTHER PUBLICATIONS

Liu et al, Oct. 2017, Frontiers in Physics, vol. 5, pp. 1-8 (Year: 2017).*
Liu et al, Chemistry, vol. 17, No. 37, pp. 10222-10225 (Year: 2011).*
Liu et al, Proceedings of the 2011 World Molecular Imaging Congress, San Diego, CA, USA, Sep. 7-10, 2011: Presentation No. P192, Poster Session 1, Sep. 7, 2011, Room: Hall F (Year: 2011).*
Liu et al, Front. Phys. Oct. 2017, vol. 5, No. 54, pp. 1-8 (Year: 2017).*
Price, Thesis: Synthesis, Evaluation, and Application of New Ligands for Radiometal Based Radiopharmaceuticals, 385 pages (Year: 2014).*
Hernandez et al, Eur. J. Nucl. Med. Mol. Imaging, vol. 42, No. 12, pp. 1859-1868 (Year: 2015).*

* cited by examiner

*Primary Examiner* — D. L. Jones
(74) *Attorney, Agent, or Firm* — DLA Piper LLP (US)

(57) ABSTRACT

A method of preparing a $^{64}$Cu-BaBaSar-RGD$_2$ solution is provided. The method includes lyophilizing a solution of BaBaSar-RGD$_2$ and adding a $^{64}$Cu solution to the lyophilized BaBaSar-RGD$_2$.

2 Claims, 7 Drawing Sheets

DGEA peptide for α2β1 receptor targeting

Dimeric RGD peptide for αvβ3 receptor targeting

Bombesin peptide for GRPR receptor targeting

ONE STEP 64CU-BABASAR-RGD2 PRODUCTION METHOD

CROSS-REFERENCE TO RELATED APPLICATIONS

This application claims benefit of priority under 35 U.S.C. § 119(e) of U.S. Ser. No. 62/593,723, filed Dec. 1, 2017, the entire contents of which is incorporated herein by reference in its entirety.

FIELD OF THE INVENTION

The present invention relates in general to the preparation of imaging probes.

BACKGROUND OF THE INVENTION

Tumor-induced angiogenesis plays a critical role in tumor progression and metastasis. Without new vasculature and blood circulation, tumor stops growing at the size of 1-2 mm3 and may become necrotic or even apoptotic since diffusion is already insufficient to supply the tissue with oxygen and nutrients (1, 2). Substantial efforts have been made to develop therapeutic strategies that interrupt the angiogenic process to stop the tumor growth (3). Integrin $\alpha v \beta 3$ is a vital component for the angiogenic process by mediating endothelial cell (EC) migration and survival during angiogenesis (4). For neovasculature formation, ECs need to migrate into an avascular region and to extensively remodel the extracellular matrix (ECM). In this process, integrins $\alpha v \beta 3$, an immunoglobulin superfamily molecule has proved to be one of the most important cell adhesion receptors for various ECM proteins. While in normal tissues, expression of integrin $\alpha v \beta 3$ is much lower, making integrin $\alpha v \beta 3$ an ideal target for diagnosis and therapy in cancer study. A protocol to non-invasively quantify its expression levels will provide a method to document integrin levels, which can support the anti-integrin $\alpha v \beta 3$ treatment for the patients, and effectively monitor treatment progress for the integrin $\alpha v \beta 3$-positive patients. Non-invasive detection and quantification of integrin $\alpha v \beta 3$ is also leading to the diagnosis of many types of cancer at their earliest stages (5).

Peptides containing Arg-Glu-Asp (RGD) amino acid sequence have a high binding affinity and selectivity for integrin $\alpha v \beta 3$ (6). In the last two decades, a number of peptides containing RGD sequences have been developed to target tumors overexpressing $\alpha_v \beta_3$ receptors (7). RGD peptides have been modified and radiolabeled for positron emission tomography (PET) probe development. $^{18}$F-galacto-RGD is the first RGD probe tested in human subjects for detecting $\alpha_v \beta_3$ expression. With conjugation of a sugar moiety for reducing the liver uptake, $^{18}$F-galacto-RGD is still specifically binding to integrin $\alpha_v \beta_3$, shows a more desirable biodistribution in humans, and provides a better visualization of $\alpha_v \beta_3$ expression in tumors with high contrast (8). However, a major disadvantage for $^{18}$F-galacto-RGD is the long and sophisticated preparation, including multiple synthetic steps that complicate routine production (9). Due to the importance of RGD peptides, continued efforts have been made to achieve desirable PET probes for easy production, optimal pharmacokinetics, and higher tumor uptake, such as $^{18}$F-AH111585 (10-12), $^{18}$F-alfatide (13,14), $^{18}$F-RGD-K5 (15,16), $^{18}$F-FPPRGD$_2$ (17,18), $^{18}$F-fluciclatide (12,19), and $^{68}$Ga-NOTA-PRGD$_2$ (20).

$^{64}$Cu ($T_{1/2}$=12.7 h; $\beta^+$ 0.653 MeV [17.8%]) has been widely used for radiolabeling proteins, antibodies and peptides for PET probe development. The low $\beta^+$ energy of $^{64}$Cu gives a resolution down to 1 mm in PET images and is important to achieve lower radiation doses for the patients (21). Cage-like hexaazamacrobicyclic sarcophagine chelator completely encapsulates the coordinated $Cu^{2+}$ ions. Their complexes exhibit enhanced thermodynamic and kinetic stability to copper-binding proteins in vivo (22). Starting from hexaazamacrobicyclic sarcophagine, a BaBaSar chelator for conjugation with RGD peptide (BaBaSar-RGD$_2$) was developed. The $^{64}$Cu labeling chemistry for BaBaSar-RGD$_2$ was achieved at room temperature to give a quantitative yield. The resulting $^{64}$Cu-BaBaSar-RGD$_2$ probe shows great stability both in vitro and in vivo, providing high tumor uptake and low normal organ uptake in U87MG glioblastoma tumor bearing mice (23). Due to the wide application of RGD peptide in diagnostic and therapeutic applications, there is a need for PET radiotracer for integrin imaging that can be made easily. Such a PET radiotracer would be of great interest to both radiochemists and physicians.

SUMMARY OF THE INVENTION

One aspect of the present invention is directed to a method of preparing a $^{64}$Cu-BaBaSar-RGD$_2$ solution. The method includes lyophilizing a solution of BaBaSar-RGD$_2$ and adding a $^{64}$Cu solution to the lyophilized BaBaSar-RGD$_2$.

In one embodiment, the $^{64}$Cu solution includes $^{64}$CuCl$_2$.

In another embodiment, the $^{64}$Cu solution includes buffer salts.

In another embodiment, the solution of BaBaSar-RGD$_2$ includes buffer salts.

In another embodiment, the buffer salts include sodium acetate buffer.

Another aspect of the present invention is directed to a method preparing a $^{64}$Cu-BaBaSar-RGD$_2$ solution. The method includes lyophilizing a $^{64}$Cu-BaBaSar-RGD$_2$ solution and reconstituting the $^{64}$Cu-BaBaSar-RGD$_2$ solution with an aqueous solution.

In one embodiment, the $^{64}$Cu-BaBaSar-RGD$_2$ solution includes buffer salts.

In another embodiment, the buffer salts include sodium acetate buffer.

Another aspect of the present invention is to provide a kit for preparing a positron emission tomography (PET) probe. The kit includes a lyophilized powder of BaBaSar-RGD$_2$ and instructions on how to reconstitute the lyophilized powder with a $^{64}$Cu solution.

In some embodiments, the $^{64}$Cu solution comprises a $^{64}$Cu$^{2+}$ salt dissolved or dispersed in a suitable liquid medium. The $^{64}$Cu solution comprises a $^{64}$Cu halide salt, wherein the halide is selected from a group that includes fluorine, chlorine, bromine and iodine.

In some embodiments, the $^{64}$Cu solution can include one or more buffer salts.

In some embodiments, the solution of BaBaSar-RGD$_2$ can include one or more buffer salts.

Other aspects and advantages of the invention will be apparent from the following description and the appended claims.

DETAILED DESCRIPTION OF THE INVENTION

Unless otherwise indicated herein, all terms used herein have the meanings that the terms would have to those skilled in the art of the present invention. Practitioners are particularly directed to current textbooks for definitions and terms of the art. It is to be understood, however, that this invention is not limited to the particular methodology, protocols, and reagents described, as these may vary.

To promote the clinical application of $^{64}$Cu-BaBaSar-RGD$_2$ in humans, the present invention provides a straightforward, one-step synthesis of $^{64}$Cu-BaBaSar-RGD$_2$ radiopharmaceutical using a preloaded cold kit.

Figure 1:
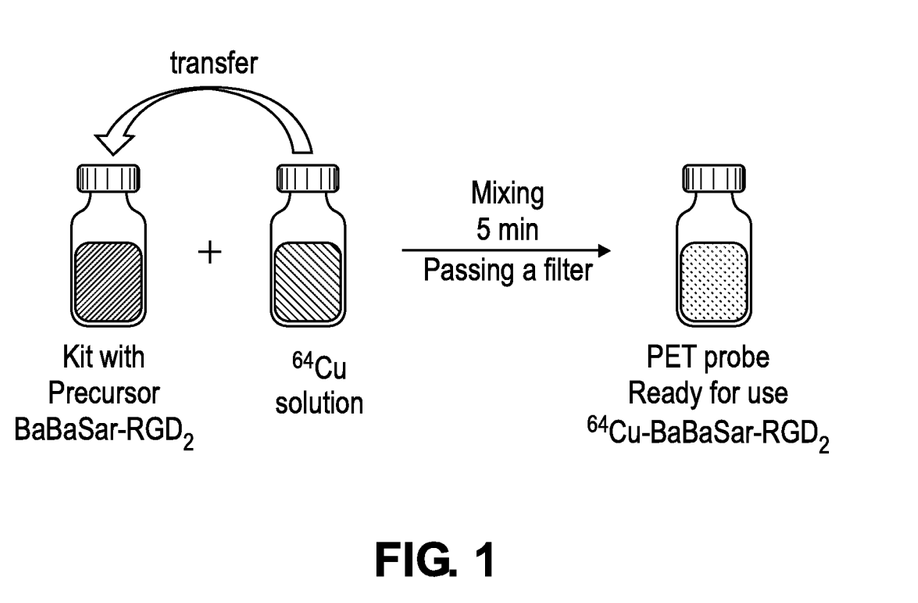
FIG. 1: Kit production process of $^{64}$Cu-BaBaSar-RGD$_2$.
Figure 5:
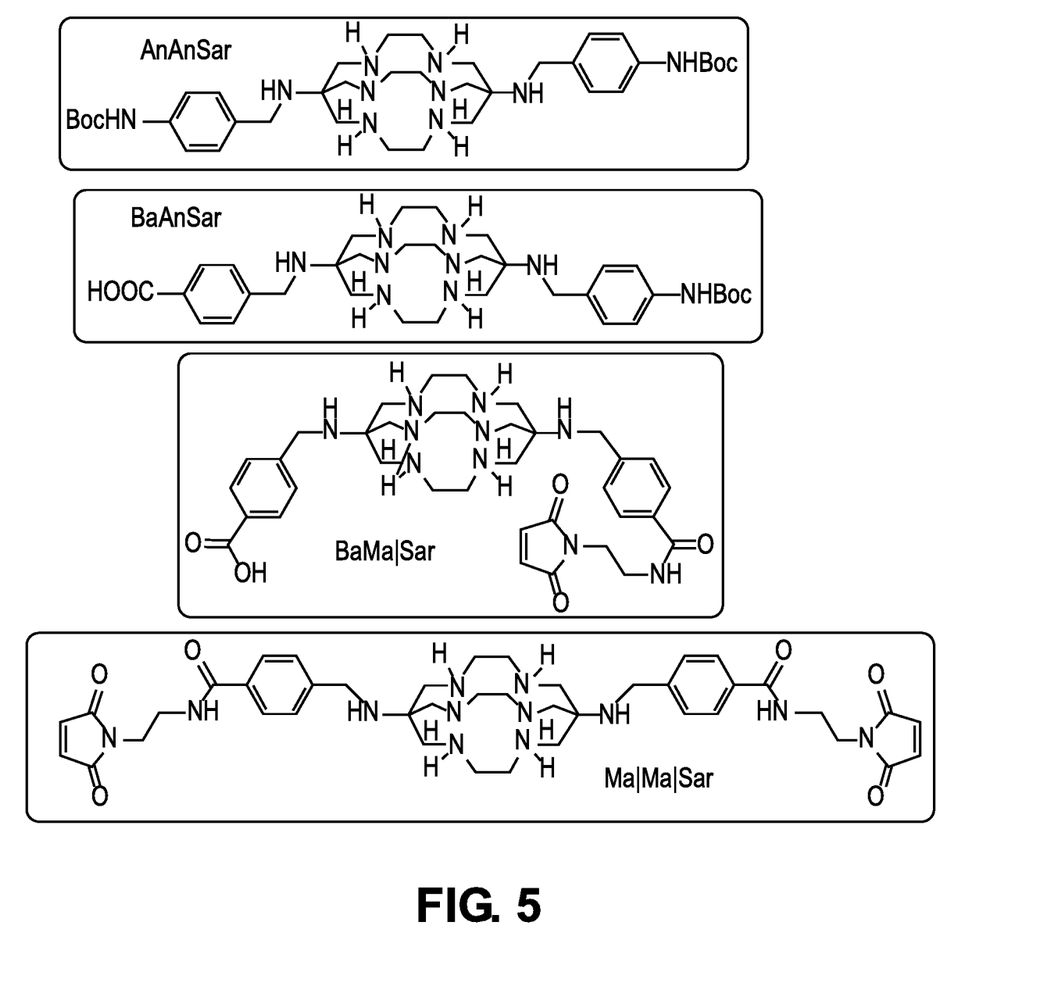
FIG. 5: Structures of AnAnSar, BaAnSar, BaMalSar, and MalMalSar.
Figure 6:
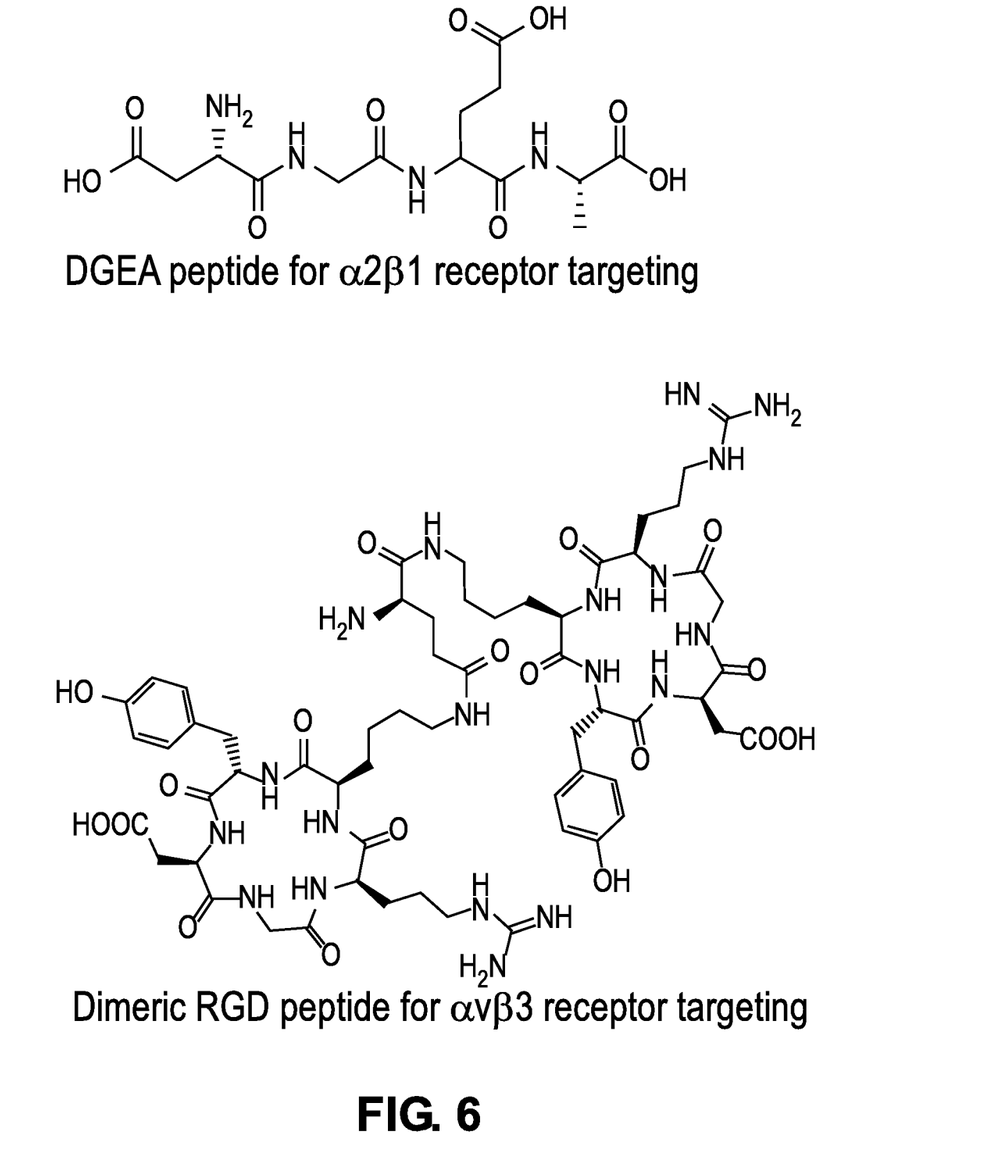
FIG. 6: Additional peptides to be used in present invention.

The present invention provides a one-step production of radiopharmaceutical $^{64}$Cu-BaBaSar-RGD$_2$ with a kit preloaded with all the precursors. FIG. 1 discloses the process of production. Furthermore, this method is not limited to the production of $^{64}$Cu-BaBaSar-RGD$_2$. When biological ligands other than RGD peptides are conjugated with the BaBaSar chelator, the same kit method associated with BaBaSar chelator could be used too. For example, other peptides can be used in place of RGD. In addition, other chelators, preferably sarcophagine based chelators, such as AnAnSar, BaAnSar, BaMalSar, and MalMalSar can be used in place of BaBaSar. Therefore, this kit method provides a universal method for $^{64}$Cu radiopharmaceutical production.

General Method

BaBaSar-RGD$_2$ was synthesized as previously reported (23). All commercial chemicals were of analytic grade and used without further purification. $^{64}$Cu in hydrochloric acid was obtained from Washington University (St. Louis, Mo.) or produced in the Molecular Imaging Center Cyclotron Facility. Analytic reversed-phase high-performance liquid chromatography (RP-HPLC) using a Phenomenex Luna column (5μ, C$_{18}$, 250×4.6 mm) were performed on a Dionex U3000 chromatography system with a diode arrays detector and radioactivity flow-count (Eckert & Ziegler, Valencia, Calif.). The recorded data were processed using Chromeleon version 7.20 software. The flow rate of analytical HPLC was 1.0 mL/min. The mobile phase starts from 95% solvent A (0.1% trifluoroacetic acid [TFA] in water) and 5% solvent B (0.1% TFA in acetonitrile [MeCN]). From 2 to 32 min, the mobile phase ramped to 35% solvent A and 65% solvent B. The ultraviolet (UV) detector of HPLC was set at 254 nm. The endotoxin analysis was performed on a portable Endosafe®-PTS™ system consisting of LAL reagent and endotoxin controls applied to a single use, polystyrene cartridge.

Radiopharmaceutical Preparation

Preparation of $^{64}$Cu-BaBaSar-RGD$_2$ Production Kit

The 18.2 MΩ·cm water from in-house GenPure™ station was treated with chelex 100 resin 48 hours before use. All the solution hereafter was prepared with this treated water. The lyophilized BaBaSar-RGD$_2$ (1.0 mg) was dissolved in 1.0 mL sodium acetate buffer (NaOAc, 0.1 M, pH 5.5). The pH of BaBaSar-RGD$_2$ solution was adjusted to pH 5.5 using 0.1 M sodium hydroxide (NaOH). Then, the BaBaSar-RGD$_2$ solution was equally aliquoted to 20 Eppendorf vials (1.5 mL). The filled vials were frozen using dry ice and then transferred to the bottles of the Labconco Freeze Dry System (pressure <100 mTorr). After the solvent was removed, the vials containing BaBaSar-RGD$_2$ powder were then sealed and stored at −18° C. for $^{64}$Cu labeling.

$^{64}$Cu-Labeling Chemistry

64CuCl2 (5-30 mCi) purchased from Washington University at St. Louis was reconstituted using 200-300 μL NaOAc buffer (0.1 M, pH 5.5) and added to a vial prepared in above section. The vial was gently shaking at room temperature for 5 min. After the reaction was quenched with 5.0 mL saline, the activity passed through a 0.22 μm sterile filter (Pall Corp.) into a 10 mL Allergy vial for quality control test and animal/human injection.

Kit Preparation

A cold kit can contain 50 μg BaBaSar-RGD$_2$ ligand to which $^{64}$CuCl$_2$ is to be complexed, and buffer salts to adjust the pH suitable for the labelling conditions. The kits are prepared in a lyophilized form and have a long shelf life of over 3 months at room temperature. When the cold kits are stored in a refrigerator at 2-8° C., the shelf life is over a year.

Radiochemistry

Figure 2:
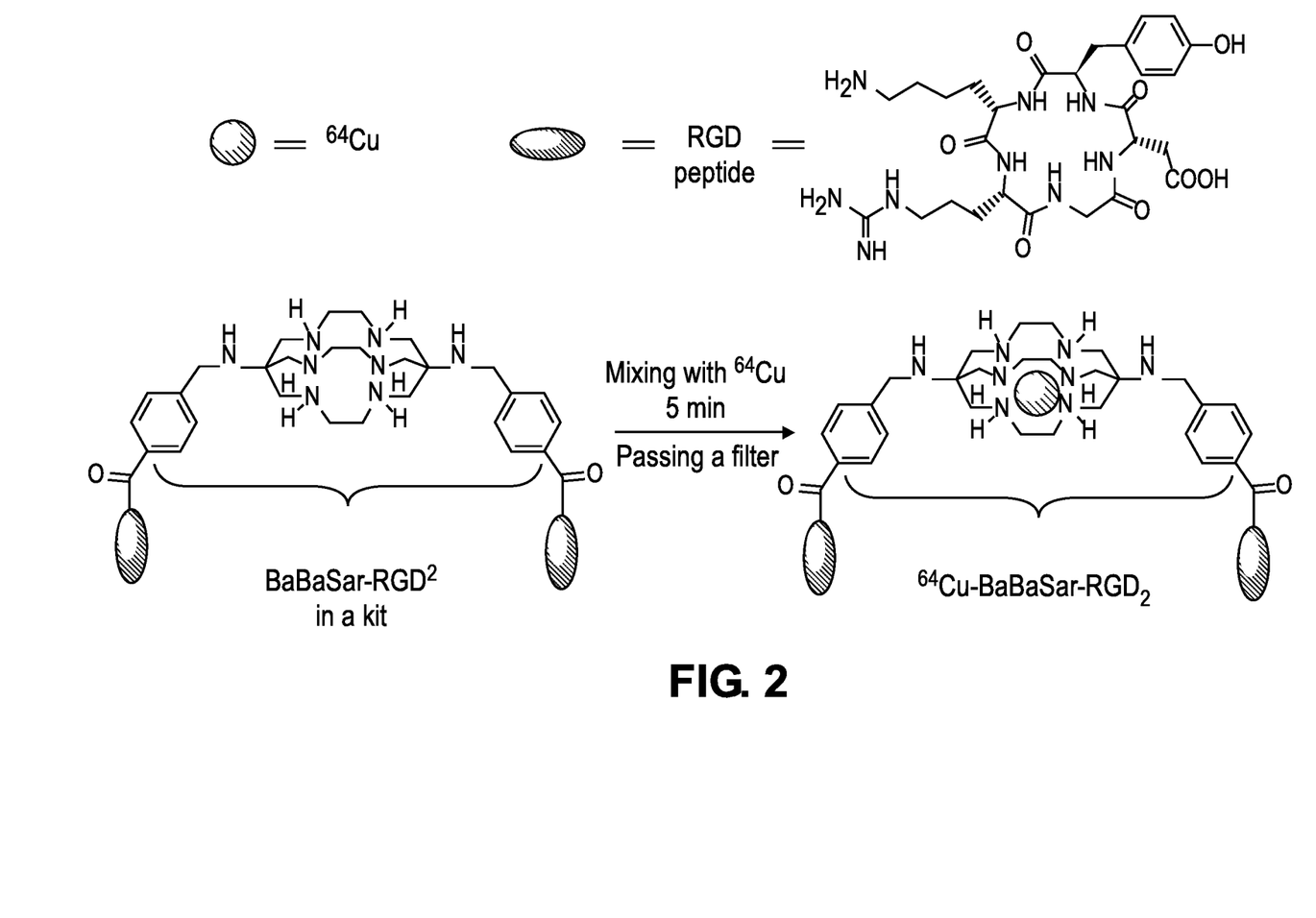
FIG. 2: Structure of RGD peptide and the synthesis route for $^{64}$Cu-BaBaSar-RGD$_2$.
Figure 3:
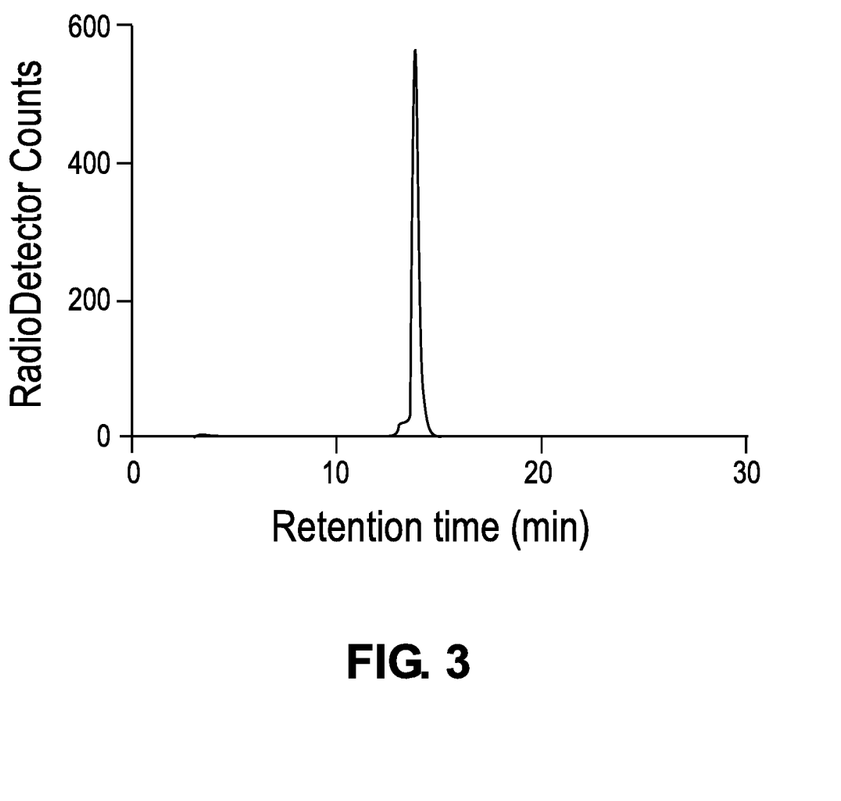
FIG. 3: Analytical radio trace HPLC chromatogram for the purity of the $^{64}$Cu-BaBaSar-RGD$_2$.

The labeling chemistry for $^{64}$Cu-BaBaSar-RGD$_2$ is disclosed in FIG. 2. The $^{64}$Cu-labeling yield for $^{64}$Cu-BaBaSar-RGD$_2$ was >99% based on HPLC analysis (FIG. 3). However, after passing through 0.22 μm Pall filter to remove pyrogen, approximately 15-20% $^{64}$Cu-BaBaSar-RGD$_2$ was trapped onto the filter and the overall recovered yield for $^{64}$Cu-BaBaSar-RGD$_2$ is about 80% calculated from the loaded $^{64}$Cu. The radiochemical purity of $^{64}$Cu-BaBaSar-RGD$_2$ was >99% based on radiotrace analytical HPLC (FIG. 3). The retention times for free $^{64}$CuCl$_2$ and $^{64}$Cu-BaBaSar-RGD$_2$ on HPLC were 2.5 and 13.9 min, respectively. The reaction crude without purifications did not show free $^{64}$Cu in HPLC chromatograms. Therefore, no further purification is needed for the final product.

Quality Control

All the quality control results met the pre-specified limits for 3 validation runs. These included half-life, appearance, pH value, identity, endotoxin amount, etc. (Table 1). The specific activity determined by HPLC analysis was between 389.2 and 605.4 mCi/μmol (average±SD, 473.0±116.2 mCi/μmol). Therefore, a human dose (<25 mCi) of $^{64}$Cu-BaBaSar-RGD$_2$ contained less than 125 μg of RGD peptide.

TABLE 1

Quality control data from 3 synthesis runs.

| QC Test | Release Criteria | Run 1 | Run 2 | Run 3 |
|---|---|---|---|---|
| Product (mCi) | none | 5.5 | 6.2 | 4.5 |
| Visual Inspection | Clear, colorless | Yes | Yes | Yes |
| Radiochemical Identity | RRT = 0.9-1.1 | 1.0 | 1.0 | 1.0 |
| Radiochemical Purity | >90% | 99% | 100% | 99% |
| Specific Activity (mCi/μmol) | >100 | 15.7 | 14.4 | 22.4 |
| Dose pH | 4.5-7.5 | 5.5 | 6.0 | 6.0 |
| Sterile Filter Integrity Test (psi) | >45 | 64 | 64 | 62 |
| Radionuclidic Identity ($t_{1/2}$) | 12.6-12.8 h | 12.7 | 12.7 | 12.7 |
| Endotoxin Analysis (EU/mL) | ≤17.5 | <5 | <5 | <5 |

Absorbed Dose Estimates from Macaque Imaging

Figure 4:
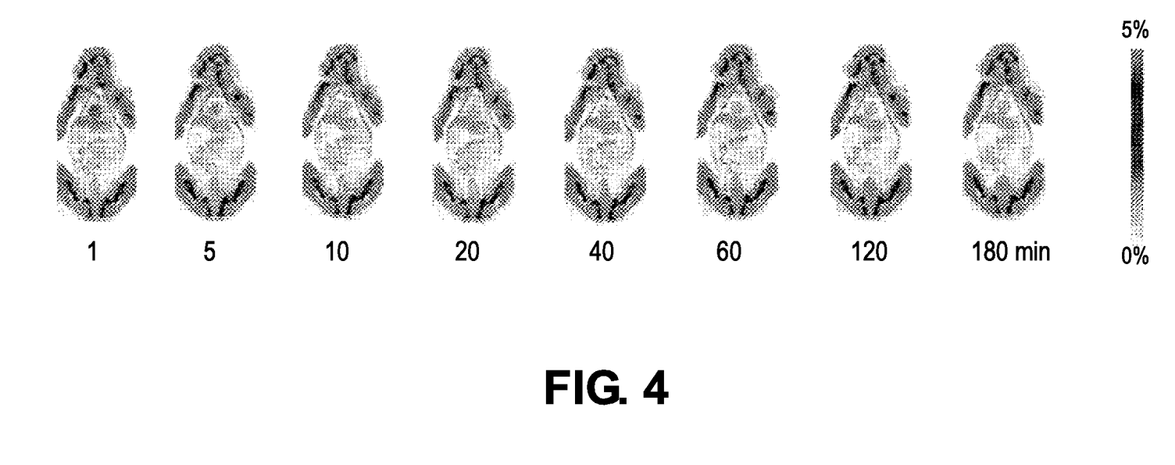
FIG. 4: Decay-corrected anterior maximum-intensity projections of PET/CT at 1, 5, 10, 20, 40, 60, 120, and 180 min after injection of $^{64}$Cu-BaBaSar-RGD$_2$ in macaque monkey.

The injection of 13.1-19.7 MBq/kg of $^{64}$Cu-BaBaSar-RGD$_2$ in macaque monkey produced no observable effects on vital signs (blood pressure, pulse, and electrocardiogram) during and 24-h after PET scan. The PET images at 1, 5, 10, 20, 40, 60, 120, and 180 min after injection are disclosed in FIG. 4. At 1 min, rapid uptake of $^{64}$Cu-BaBaSar-RGD$_2$ was observed in the heart, and liver. The bladder content was visualized at 10 min after injection and more and more activity was accumulated in urine bladder content. The bladder did not void because the macaque monkey was under anesthesia. Gallbladder uptake was not observed during the whole scan. Rapid clearance of activity in the liver was observed in the images at time points after 1 min. The urinary bladder had the highest uptake, with 51.37%±8.73% of injected activity at 1 h post injection. The maximum uptake for the liver, and kidneys were 37.40±6.63% ID (9 min) and 26.79±4.35% ID (0.5 min) respectively. At 3 h of post injection, 8.62%±1.41% of injected activity was found in the gallbladder, small intestine, and upper and lower portions of the large intestine.

The mean organ doses for the male human phantom were calculated with Olinda/EXM using $^{64}$Cu-BaBaSar-RGD$_2$ biodistribution in monkey (Table 2). The kidneys had the highest radiation-absorbed doses (108.43 µGy/MBq), followed by the bladder wall (87.07 µGy/MBq). The mean effective dose of $^{64}$Cu-BaBaSar-RGD$_2$ was 15.30±2.21 µSv/MBq. When 925-MBq of $^{64}$Cu-BaBaSar-RGD$_2$ is administrated into human subject, the effective dose for the non-voiding model is estimated to be 14.2 mSv, which is comparable to the estimated 6.23 mSv dose in a whole-body PET scan with 2-deoxy-2-[$^{18}$F]fluoro-D-glucose ($^{18}$F-FDG) (24). The estimated doses for the female human were higher by 18% because body and organ sizes of women are smaller than those men (data not shown).

Venous blood samples were withdrawn from monkey during the PET scan. Based on the decay corrected activity per unit of blood sample, it was found that $^{64}$Cu-BaBaSar-RGD$_2$ was cleared rapidly from the blood. By 3 h after injection, 2.88±0.88% ID remained (range, 2.07-3.82% ID). At 22 h after injection, the activity in the blood decreased to 0.79±0.52% ID. Based on the percentage of injected dose in blood sample, the half life of $^{64}$Cu-BaBaSar-RGD$_2$ in blood pool was calculated as 12.1±4.0 min (n=3).

TABLE 2

Estimated Human Absorbed Doses of $^{64}$Cu-BaBaSar-RGD$_2$ to Normal Organs Using Biodistribution Data from Macaque monkey.

| Organs | Mean ± SD (µGy/MBq) |
| --- | --- |
| Adrenals | 3.34 ± 0.52 |
| Brain | 1.27 ± 0.22 |
| Breasts | 1.34 ± 0.23 |
| Gall bladder Wall | 3.07 ± 0.49 |
| LLI Wall | 2.86 ± 0.44 |
| Small Intestine | 4.53 ± 0.68 |
| Stomach Wall | 2.11 ± 0.34 |
| ULI Wall | 2.47 ± 0.39 |
| Heart Wall | 4.39 ± 0.62 |
| Kidneys | 108.43 ± 16.41 |
| Liver | 7.54 ± 1.15 |
| Lungs | 1.67 ± 0.28 |
| Muscle | 1.88 ± 0.31 |
| Ovaries | 2.88 ± 0.44 |
| Pancreas | 2.86 ± 0.45 |
| Red Marrow | 9.29 ± 1.02 |
| Osteogenic Cells | 7.01 ± 0.91 |
| Skin | 1.38 ± 0.24 |
| Spleen | 6.78 ± 0.88 |
| Testes | 2.03 ± 0.33 |
| Thymus | 1.56 ± 0.26 |
| Thyroid | 1.39 ± 0.24 |
| Urinary Bladder Wall | 87.07 ± 12.38 |
| Uterus | 4.16 ± 0.63 |
| Total Body | 2.76 ± 0.42 |
| Effective Dose* | 15.30 ± 2.21 |

*In unit of µSv/MBq

Integrin αvβ3-targeted radiopharmaceutical $^{64}$Cu-BaBaSar-RGD$_2$ has been successfully synthesized with the one-step kit method. The straightforward method greatly simplifies the production process and benefits the clinical application of $^{64}$Cu-BaBaSar-RGD$_2$. Human radiation dosimetry of $^{64}$Cu-BaBaSar-RGD$_2$ was estimated after intravenous administration in macaque monkey, by PET imaging and OLINDA/EXM calculations. The critical organs were kidneys and urinary bladder wall. The mean effective dose, determined with the male adult model, was 15.30±2.21 Sv/MBq. This PET probe demonstrates an acceptable radiation dose comparable to other reported RGD-derived radiopharmaceuticals. These demonstrate great promise of $^{64}$Cu-BaBaSar-RGD$_2$ as an integrin marker, with a desirable biodistribution and safety characteristics in monkey. Therefore, $^{64}$Cu-BaBaSar-RGD$_2$ can safely be used in human scan for further evaluation of its performance as an integrin-targeting probe.

REFERENCES

All references cited herein, including those below and including but not limited to all patents, patent applications, and non-patent literature referenced below or in other portions of the specification, are hereby incorporated by reference herein in their entirety.

1. Holmgren L, O'Reilly M S, Folkman J. Dormancy of micrometastases: balanced proliferation and apoptosis in the presence of angiogenesis suppression. *Nat Med.* 1995; 1:149-153.
2. Parangi S, O'Reilly M, Christofori G, Holmgren L, Grosfeld J, Folkman J, Hanahan D. Antiangiogenic therapy of transgenic mice impairs de novo tumor growth. *Proc Natl Acad Sci USA.* 1996; 93:2002-2007.
3. Brown A P, Citrin D E, Camphausen K A. Clinical biomarkers of angiogenesis inhibition. *Cancer Metastasis Rev.* 2008; 27:415-434.
4. Brooks P C, Montgomery A M, Rosenfeld M, Reisfeld R A, Hu T, Klier G, Cheresh D A. Integrin alpha v beta 3 antagonists promote tumor regression by inducing apoptosis of angiogenic blood vessels. *Cell.* 1994; 79:1157-1164.
5. Marelli U K, Rechenmacher F, Sobahi T R, Mas-Moruno C, Kessler H. Tumor Targeting via Integrin Ligands. *Front Oncol.* 2013; 3:222.
6. Plow E F, Haas T A, Zhang L, Loftus J, Smith J W. Ligand binding to integrins. *J Biol Chem.* 2000; 275:21785-21788.
7. Liu S. Radiolabeled Cyclic RGD Peptide Bioconjugates as Radiotracers Targeting Multiple Integrins. *Bioconjug Chem.* 2015; 26:1413-1438.
8. Beer A J, Haubner R, Wolf I, Goebel M, Luderschmidt S, Niemeyer M, Grosu A L, Martinez M J, Wester H J, Weber W A, Schwaiger M. PET-based human dosimetry of 18F-galacto-RGD, a new radiotracer for imaging alpha v beta3 expression. *J Nucl Med.* 2006; 47:763-769.
9. Haubner R, Kuhnast B, Mang C, Weber W A, Kessler H, Wester H J, Schwaiger M. [18F]Galacto-RGD: synthesis, radiolabeling, metabolic stability, and radiation dose estimates. *Bioconjug Chem.* 2004; 15:61-69.
10. Morrison M S, Ricketts S A, Barnett J, Cuthbertson A, Tessier J, Wedge S R. Use of a novel Arg-Gly-Asp radioligand, 18F-AH111585, to determine changes in tumor vascularity after antitumor therapy. *J Nucl Med.* 2009; 50:116-122.
11. McParland B J, Miller M P, Spinks T J, Kenny L M, Osman S, Khela M K, Aboagye E, Coombes R C, Hui A M, Cohen P S. The biodistribution and radiation dosimetry of the Arg-Gly-Asp peptide 18F-AH111585 in healthy volunteers. *J Nucl Med.* 2008; 49:1664-1667.
12. Kenny L M, Coombes R C, Oulie I, Contractor K B, Miller M, Spinks T J, McParland B, Cohen P S, Hui A M, Palmieri C, Osman S, Glaser M, Turton D, Al-Nahhas A, Aboagye E O. Phase I trial of the positron-emitting Arg-Gly-Asp (RGD) peptide radioligand 18F-AH111585 in breast cancer patients. *J Nucl Med.* 2008; 49:879-886.
13. Zhou Y, Gao S, Huang Y, Zheng J, Dong Y, Zhang B, Zhao S, Lu H, Liu Z, Yu J, Yuan S. A Pilot Study of 18F-Alfatide PET/CT Imaging for Detecting Lymph Node Metastases in Patients with Non-Small Cell Lung Cancer. *Sci Rep.* 2017; 7:2877.
14. Wan W, Guo N, Pan D, Yu C, Weng Y, Luo S, Ding H, Xu Y, Wang L, Lang L, Xie Q, Yang M, Chen X. First experience of 18F-alfatide in lung cancer patients using a new lyophilized kit for rapid radiofluorination. *J Nucl Med.* 2013; 54:691-698.
15. Mirfeizi L, Walsh J, Kolb H, Campbell-Verduyn L, Dierckx R A, Feringa B L, Elsinga P H, de Groot T, Sannen I, Bormans G, Celen S. Synthesis of [18F]RGD-K5 by catalyzed [3+2] cycloaddition for imaging integrin alphavbeta3 expression in vivo. *Nucl Med Biol.* 2013; 40:710-716.
16. Doss M, Kolb H C, Zhang J J, Belanger M J, Stubbs J B, Stabin M G, Hostetler E D, Alpaugh R K, von Mehren M, Walsh J C, Haka M, Mocharla V P, Yu J Q. Biodistribution and radiation dosimetry of the integrin marker 18F-RGD-K5 determined from whole-body PET/CT in monkeys and humans. *J Nucl Med.* 2012; 53:787-795.
17. Iagaru A, Mosci C, Mittra E, Zaharchuk G, Fischbein N, Harsh G, Li G, Nagpal S, Recht L, Gambhir S S. Glioblastoma Multiforme Recurrence: An Exploratory Study of (18)F FPPRGD2 PET/CT. *Radiology.* 2015; 277:497-506.
18. Iagaru A, Mosci C, Shen B, Chin F T, Mittra E, Telli M L, Gambhir S S. (18)F-FPPRGD2 PET/CT: pilot phase evaluation of breast cancer patients. *Radiology.* 2014; 273:549-559.
19. Mena E, Owenius R, Turkbey B, Sherry R, Bratslavsky G, Macholl S, Miller M P, Somer E J, Lindenberg L, Adler S, Shih J, Choyke P, Kurdziel K. [(1)(8)F]fluciclatide in the in vivo evaluation of human melanoma and renal tumors expressing alphavbeta 3 and alpha vbeta 5 integrins. *Eur J Nucl Med Mol Imaging.* 2014; 41:1879-1888.
20. Li D, Zhao X, Zhang L, Li F, Ji N, Gao Z, Wang J, Kang P, Liu Z, Shi J, Chen X, Zhu Z. (68)Ga-PRGD2 PET/CT in the evaluation of Glioma: a prospective study. *Mol Pharm.* 2014; 11:3923-3929.
21. Chatziioannou A, Tai Y C, Doshi N, Cherry S R. Detector development for microPET II: a 1 microl resolution PET scanner for small animal imaging. *Phys Med Biol.* 2001; 46:2899-2910.
22. Smith S V. Molecular imaging with copper-64. *J Inorg Biochem.* 2004; 98:1874-1901.
23. Liu S, Li Z, Yap L P, Huang C W, Park R, Conti P S. Efficient preparation and biological evaluation of a novel multivalency bifunctional chelator for $^{64}$Cu radiopharmaceuticals. *Chemistry.* 2011; 17:10222-10225.
24. Huang B, Law M W, Khong P L. Whole-body PET/CT scanning: estimation of radiation dose and cancer risk. *Radiology.* 2009; 251:166-174.
25. U.S. Pat. No. 9,789,211.

What is claimed is:

1. A method of preparing a $^{64}$Cu-BaBaSar-RGD$_2$ solution comprising:
    lyophilizing a solution of BaBaSar-RGD$_2$ comprising a buffer salt to obtain a powder of BaBaSar-RGD$_2$ and the buffer salt; and
    adding a $^{64}$Cu solution comprising $^{64}$CuCl$_2$ to the powder of BaBaSar-RGD$_2$ and the buffer salt.
2. The method of claim 1, wherein the buffer salt is sodium acetate buffer.

* * * * *